Oct. 5, 1937. J. D. BROWNELL Plant Pat. 263
ROSE
Filed Sept. 15, 1936
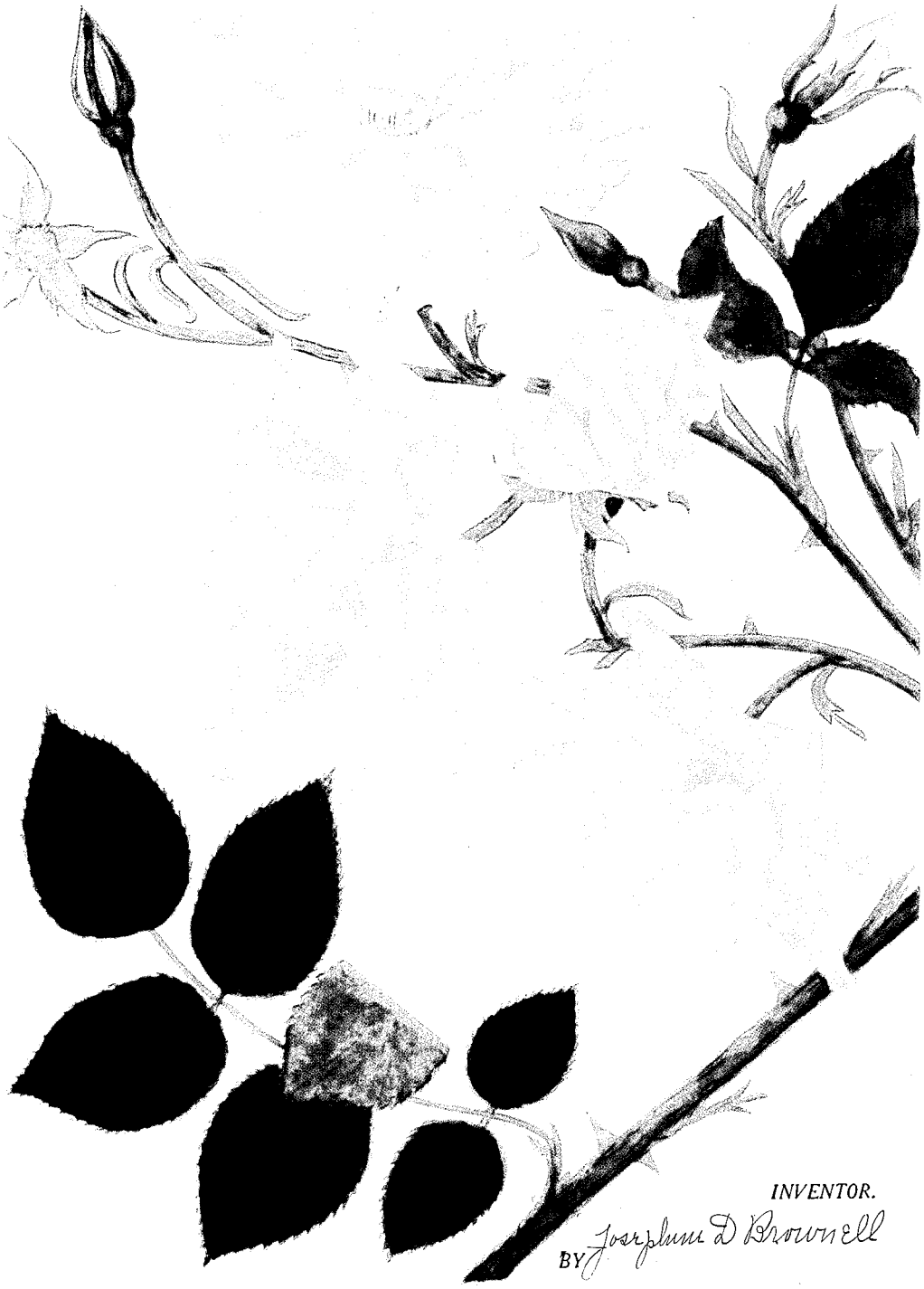
INVENTOR.
BY Josephine D Brownell
ATTORNEY.

Patented Oct. 5, 1937

Plant Pat. 263

UNITED STATES PATENT OFFICE

263

ROSE

Josephine D. Brownell, Little Compton, R. I.

Application September 15, 1936, Serial No. 100,890

1 Claim. (Cl. 47—61)

My invention relates to roses and especially to a new, original and distinct variety, of the class known commercially as "Hardy climbing roses", produced by me in my breeding grounds or research gardens in Little Compton, Rhode Island, and under my directions by propagation, cross, self and open pollination, which can be and has been asexually reproduced.

My new rose is new as to the following characteristics and especially as to their joint association in connection with the characteristics of hardiness or immunity from serious injury on account of cold temperatures prevailing in certain parts of the northern portion of the United States:—

The unique yellow shades of color of the petals, being in the aggregate nearly spectrum yellow (ordinary dictionary definition), with variations to slightly lighter toward the terminal borders and diffused with trace of red on the base of the opening petals and their tendency to hold those shades of yellow color under exposure and the notable opalescent or metallic luster thereof;

The novelty and variation within certain definite limits of the form of the bloom;

Its intensity and character of fragrance, and

Its climbing and branching habit.

In the accompanying drawing forming a part of this specification I have shown my new rose in its natural colors, that is, as near as is possible to do so artificially.

I otherwise describe my new rose plant as follows:

My new rose plant is a hardy hybrid climbing *Rosa wichuraiana*, crossed in its ancestral generations with, in addition to *Rosa wichuraiana*, several so called hybrid tea and species roses. My new rose plant is otherwise described as follows.

*Essential information*

Type:

Hardy climbing, outdoor; seedling; for cut flowers and garden decoration.

Class:

Hybrid climbing *wichuraiana*.

Breeding or discovery:

The pollination which produced my new rose was directed by me and made July 1, 1931* in my research garden; this seed germinated and was planted in February 1932 at the Boyce Thompson Institute for Plant Research, Inc. in Yonkers, New York State. The plant therefrom was transferred and planted in my said garden in the spring of 1932. This plant can be and has been by me and under my direction, asexually reproduced by budding in my said gardens and elsewhere during the months of July in the years 1932 to 1935 inclusive; these propagations reproduced the characters of the original seedling.

The genealogy of my new rose is to the best of my knowledge and belief as follows: This rose plant was bred and discovered by me and under my directions, by propagation and cross pollination. It is a seedling which was produced from a seed born on a climbing rose plant grown by me in my research gardens at Little Compton, Rhode Island; the variety is known commercially as Glendale. The seed was produced by me and under my direction by emasculating a flower, covering it with a bag as protection from self and foreign pollen, the pollen used in the cross was applied with a camel's hair brush and the bag promptly replaced. The pollen used in the cross was from a climbing rose plant grown by me for several years, in my breeding grounds at Little Compton, Rhode Island and was there produced by me and under my directions by cross pollination, made in the same manner as above described, the seed parent being Mary Wallace and the pollen parent being a hybrid tea there grown by me for several years; the variety is known to me but is not definitely identified by me as a commercial variety and by whom produced is unknown to me.

My new rose plant and flower seemed to me to be of unusual merit and I have since made extensive propagations thereof and tests of the variety.

It has held its distinguishing characteristics through succeeding propagations by budding.

*Flower*

Habit:

It blooms outdoors in Little Compton, Rhode Island in late June and July and begins to bloom about the same time as the climbing rose "Glendale" begins to bloom, and blooms thereafter in a lesser degree until frost.

Flowers borne:

Singly to fifteen, occasionally more; in regular hybrid tea cluster, usually on very strong, woody, stiff and frequently very large stems.

Quantity of bloom:

Abundant outdoors in full sunshine, not noticeably reduced by covering with earth for winter protection; in greenhouse, free.

Continuity:

One season of three to five weeks according to age and size of plants, with possibility of re-

*This and other dates herein are approximate.

blooming to a limited extent when established.

Fragrance:

China tea crossed with *Rosa wichuraiana* in part, notably pleasing and intense under favorable environment.

Bud:

Size medium, long pointed and opens well being little affected by either wet or hot weather.

Peduncle medium in length; medium to heavy, erect to stiff, medium green, almost smooth, few red to greenish hairs.

Foliaceous appendages occasionally extending beyond the tips of the bud equal to ¼ to ½ its length.

Color as calyx breaks is, on both sides of petals upper edges Pinard Yellow to one quarter toward Picric Yellow, shading to Empire Yellow to one quarter toward Pale Lemon Yellow, shading near the base Lemon Yellow and to Lemon Chrome. Color references are to Ridgway, Plate IV. The color intensity is slightly variable from greater to the foregoing, to less, on blooms on the same plant and on different plants under different environment, the foregoing being a substantial average of that variability under favorable conditions, with notable brilliance and opalescent or metallic luster and an unusually clear light center when sufficiently open to show anthers. The outer petal occasionally carries a slight splash of nearly Spectrum Red, Plate I.

Bloom:

Is 3½ to 5 inches in diameter when fully open, infrequently more or less; double having petals variable in number usually varying around an average of 28. The flower opens high centered, recurled, showing pistils and stamens somewhat, when fully opened. The petals have a notable character under normal temperatures of closing to nearly bud form at night to re-open in the morning; this procedure frequently repeats on two or three nights with the same bloom in a diminishing degree. Petals are in form somewhat variable, being nearly orbicular to obovate to nearly ovate, outer petals usually recurled outward and frequently with slightly waving edges, inner petals averaging narrower, to innermost petals frequently irregular to informal petaloids. Texture medium, thick, substantial and leathery, both sides slightly satiny to shiny and having a metallic luster.

Color of opening flowers picked at Little Compton, Rhode Island, July 1st, 1935 out of doors, same as the bud colors above described except that after exposure to light for one day the upper or lighter colors described extend slightly downward until after an average of about five days, each successive color described has been supplanted to an extent of somewhat more than half by the color next above it as described, at which time the petals usually fall, having lost on the average slightly more than one half of the original color described.

There is a slight difference in the color or various portions of the petals as the flowers open, but the total color effect is very much more nearly a self than a two toned effect.

The petals usually drop off cleanly, though occasionally one to three small petaloids or petals cling and turn light brown to drop off later.

Reproductive organs:

The stamens are variable, usually moderate to few of uneven length with light orange to buff anthers (ordinary dictionary definitions of colors).

Filaments mostly medium long.

Pistils are several, of slightly uneven length.

Styles are light greenish yellow to nearly white.

Stigmas are light greenish yellow.

Ovaries do not under normal conditions protrude from the calyx lobe.

*Plant*

Foliage:

This plant has the unusual habit just prior to bloom time of dropping the leaf at the base union of the bloom stem (flowering branch) with the cane or next larger branch; the balance of the foliage is notably persistent until unusually late in the fall.

The foliage is very abundant, of compound leaves of three leaflets near the flower and five leaflets farther down the stems (flowering branches) and frequently seven near the base of the stems and except in rare instances, on the canes and branches. The leaflets are nearly round to oval, with moderately acute apex, base rounded to slightly acute and slightly irregularly serrate.

Color of the upper surface is very slightly variable around Deep Dull Yellow-Green (I) during midseason, the older leaves turning toward fall to Dark Dull Yellow-Green and in the late fall to slightly darker, Plate XXXII. The undersurface is Pois Green to Asphodel Green, Plate XLI, edges of young growth slightly tinged reddish, progressively diminishing and nearly disappearing at full maturity.

The petiole and rachis are moderately slender with traces of red on the top, disappearing at maturity, and with reddish and greenish hairs on the top and prickles on the underside, reddish to pinkish turning nearly white with age. The stipules are medium long, usually around ¾ of an inch, frequently ¼ inch wide, with relatively short narrow points that spread at angles variously from 40 to 50 degrees; the edges are hairy.

The plant is unusually resistant to blackspot and mildew.

Growth:

*Habit.*—Climbing, branching.

*Growth.*—Vigorous to very vigorous. The bush is very vigorous, in comparison with Climbing Dr. W. Van Fleet is about 15% more vigorous and in comparison with American Pillar is about 20% less vigorous. It grows canes in one season on plants budded the previous season under favorable conditions to thirteen feet, and frequently grows branches therefrom the same season.

*Canes.*—Medium to nearly heavy. The canes are large and stiff yet bend freely without breaking in forming top growth on two year old plants lifted from the field and bent to 12 to 14 inches from the top of the pot for greenhouse forcing. The color of the new grown bark on the stems is green with reddish shadings and reddish prickles pointed slightly backward.

*Mature stems.*—Green shadings from nearly the color of the underside of the leaflets slightly toward the color of the upper sides of the leaflets, with a shading of reddish overlay frequently, where exposed during growth to sunlight, younger growth shading on the sides exposed to sunlight, to the color of the marginal edges of the young leaflets.

*Prickles.*—Several, nearly straight, color nearly Dragon's-blood Red, shading toward tip to Coral Pink, Plate XIII.

*Hairs.*—None except on peduncle.

*New shoots.*—Same as above for young growth to slightly lighter.

Winter resistance:

From limited tests made at Little Compton, Rhode Island, it would seem that this variety is resistant exposed to about twelve degrees below zero Fahrenheit to bloom normally at the following bloom time; that temperatures as low as about twenty-three degrees below zero will kill back the wood to nearly the level of protection.

Comparisons:

There is no hardy climbing rose in commerce known to me that is closely comparable with my new rose. Le Reve (Pernet Ducher, 1923) is the nearest in color, at Little Compton, Rhode Island; it is slightly less near spectrum yellow and slightly less brilliant, it is less recurled in form, very much less pleasing in fragrance, its foliage is less persistent, usually falling two to three months earlier, less in substance and depth of color, it blooms usually only after two years of growth after planting as a two year old plant while my variety usually blooms freely after one such year of growth and frequently blooms somewhat as a two year old transplant the bloom season of planting and occasionally on a break from eye budded the previous season.

Star of Persia is nearly similarly compared as to foliage and the bloom color contains very much more red, and the size and form of the blooms are less and inferior as to H. T. type as compared with my variety. It is also incomparable as to vigor in Little Compton, Rhode Island.

Climbing Primrose is imbricated, having several times as many petals that open without the H. T. character form of my rose. It is lacking in vigor and winter resistance as compared with my variety at Little Compton, Rhode Island and the foliage is lighter in color and less persistent.

Easlea's Golden Rambler lacks about 50% of the yellow contained in my variety as grown at Little Compton, Rhode Island and compares unfavorably much similar to the above varieties as to fragrance, bloom form, and foliage characters; the flower under various conditions is not as long lasting.

I claim:—

The hardy hybrid *Rosa wichuraiana* climbing rose plant, with hybrid tea type of bloom as disclosed, characterized by its resistance to moderate sub-zero temperatures, in association with its China tea crossed with *Rosa wichuraiana* fragrance, with form and color substantially as shown, with its notable opalescent or metallic luster, being nearly spectrum yellow in total color effect.

JOSEPHINE D. BROWNELL.